(12) United States Patent
Mundis, Jr. et al.

(10) Patent No.: US 11,051,860 B2
(45) Date of Patent: Jul. 6, 2021

(54) SPINAL CONSTRUCT WITH FLEXIBLE MEMBER

(71) Applicant: K2M, Inc., Leesburg, VA (US)

(72) Inventors: Gregory Mundis, Jr., San Diego, CA (US); Han Jo Kim, New York, NY (US); John Ferguson, Auckland (NZ); Laurel Blakemore, Williston, FL (US); Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 56 days.

(21) Appl. No.: 16/396,026

(22) Filed: Apr. 26, 2019

(65) Prior Publication Data

US 2019/0247100 A1 Aug. 15, 2019

Related U.S. Application Data

(63) Continuation of application No. 15/730,325, filed on Oct. 11, 2017, now Pat. No. 10,292,740, which is a
(Continued)

(51) Int. Cl.
*A61B 17/88* (2006.01)
*A61B 17/70* (2006.01)
(Continued)

(52) U.S. Cl.
CPC ...... *A61B 17/7083* (2013.01); *A61B 17/0401* (2013.01); *A61B 17/7022* (2013.01);
(Continued)

(58) Field of Classification Search
CPC ............ A61B 17/7083; A61B 17/0401; A61B 17/7022; A61B 17/7049; A61B 17/7053;
(Continued)

(56) References Cited

U.S. PATENT DOCUMENTS 5,242,446 A * 9/1993 Steffee ............... A61B 17/7001
248/231.9
6,045,573 A 4/2000 Wenstrom, Jr. et al.
(Continued)

FOREIGN PATENT DOCUMENTS

EP 0582857 A1 2/1994
EP 1192908 A2 4/2002

OTHER PUBLICATIONS

U.S. Appl. No. 14/644,428, Title: Inserter and Method for Securing an Implant to a Spinal Process With a Flexible Fastening System, Filed: Mar. 11, 2015, now U.S. Pat. No. 9,757,167.
(Continued)

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

A system for securing a flexible member to a vertebra includes a flexible member, a fixation member, and an inserter. The flexible member includes two ends. The fixation member includes a head and a shank that defines a longitudinal axis of the fixation member. The head defines a slot that passes through the head orthogonal to the longitudinal axis. The slot receives a portion of the flexible member. The inserter includes a handle and a tubular member that has proximal and distal end portion. The proximal end portion is attached to the handle and the distal end portion extends from the handle. The tubular member defines a passage between the proximal and distal end portions. The distal end portion includes a couple for receiving the head of the fixation member with the portion of the flexible member received in the slot of the flexible member.

19 Claims, 9 Drawing Sheets

Related U.S. Application Data continuation of application No. 15/135,770, filed on Apr. 22, 2016, now Pat. No. 9,795,421.

(60) Provisional application No. 62/189,261, filed on Jul. 7, 2015.

(51) Int. Cl.
  *A61B 17/04* (2006.01)
  *A61B 17/86* (2006.01)

(52) U.S. Cl.
  CPC ...... *A61B 17/7049* (2013.01); *A61B 17/7053* (2013.01); *A61B 17/7082* (2013.01); *A61B 17/8869* (2013.01); *A61B 17/8605* (2013.01)

(58) Field of Classification Search
  CPC ............ A61B 17/7082; A61B 17/8869; A61B 17/8605
  USPC ....... 606/254, 263, 279, 321, 99, 104, 86 A, 606/250–253
  See application file for complete search history.

(56) References Cited

U.S. PATENT DOCUMENTS

| | | | |
|---|---|---|---|
| 6,149,653 A | 11/2000 | Deslauriers | |
| 6,159,235 A | 12/2000 | Kim | |
| 6,436,099 B1 | 8/2002 | Drewry et al. | |
| 7,285,121 B2 | 10/2007 | Braun et al. | |
| 7,344,539 B2 | 3/2008 | Serhan et al. | |
| 7,481,828 B2 | 1/2009 | Mazda et al. | |
| 7,645,293 B2 * | 1/2010 | Martinek | A61B 17/062 606/232 |
| 7,862,590 B2 | 1/2011 | Lim et al. | |
| 7,909,826 B2 | 3/2011 | Serhan et al. | |
| 7,959,654 B2 | 6/2011 | Mazda et al. | |
| 8,167,915 B2 | 5/2012 | Ferree et al. | |
| 8,172,843 B2 | 5/2012 | Baccelli et al. | |
| 8,308,771 B2 | 11/2012 | Bennett et al. | |
| 8,323,294 B2 | 12/2012 | Mickiewicz et al. | |
| 8,403,971 B2 | 3/2013 | Barrus et al. | |
| 8,480,712 B1 * | 7/2013 | Samuel | A61B 17/8605 606/250 |
| 8,814,919 B2 | 8/2014 | Barrus et al. | |
| 8,926,668 B2 | 1/2015 | Douget | |
| 8,936,625 B2 | 1/2015 | Larroque-Lahitette et al. | |
| 8,961,565 B2 | 2/2015 | Barrus et al. | |
| 9,757,167 B2 | 9/2017 | Hsu et al. | |
| 9,795,421 B2 | 10/2017 | Mundis, Jr. et al. | |
| 2001/0034522 A1 | 10/2001 | Frigg | |
| 2001/0037131 A1 | 11/2001 | Schmieding et al. | |
| 2006/0025769 A1 * | 2/2006 | Dick | A61B 17/7077 606/86 A |
| 2006/0058789 A1 * | 3/2006 | Kim | A61B 17/705 606/914 |
| 2007/0073293 A1 | 3/2007 | Martz et al. | |
| 2008/0300599 A1 | 12/2008 | Anapliotis et al. | |
| 2009/0234387 A1 | 9/2009 | Miller et al. | |
| 2010/0305576 A1 | 12/2010 | Ferguson et al. | |
| 2011/0178554 A1 | 7/2011 | Walder et al. | |
| 2011/0270314 A1 | 11/2011 | Mueller et al. | |
| 2013/0012955 A1 | 1/2013 | Lin | |
| 2013/0041410 A1 | 2/2013 | Hestad et al. | |
| 2013/0072983 A1 * | 3/2013 | Lindquist | A61B 17/7034 606/278 |
| 2014/0094850 A1 | 4/2014 | Clement et al. | |
| 2014/0163616 A1 | 6/2014 | Sojka et al. | |
| 2014/0257397 A1 | 9/2014 | Akbarnia et al. | |
| 2014/0257401 A1 * | 9/2014 | George | A61B 17/7041 606/278 |
| 2016/0051286 A1 * | 2/2016 | Gordon | A61B 17/705 606/264 |

OTHER PUBLICATIONS

Australian Search Report for Application No. 2016291125, dated Mar. 19, 2020, 1 page.
Supplementary European Search Report including Written Opinion for Application No. EP16821956.6, dated Feb. 19, 2019, pp. 1-11.
International Preliminary Report on Patentability dated Jan. 9, 2018, issued in PCT/US2016/041268.
International Search Report including Written Opinion dated Oct. 4, 2016, issued in PCT/US16/41268.
U.S. Appl. No. 62/152,325, filed Apr. 24, 2015, inventor Blakemore et al.

\* cited by examiner

SPINAL CONSTRUCT WITH FLEXIBLE MEMBER

CROSS-REFERENCE TO RELATED APPLICATIONS

This application is a continuation of U.S. patent application Ser. No. 15/730,325, filed Oct. 11, 2017, which is a continuation of U.S. patent application Ser. No. 15/135,770, filed Apr. 22, 2016, which claims the benefit of, and priority to, U.S. Provisional Patent Application Ser. No. 62/189,261, filed Jul. 7, 2015. The entire contents of each of the above disclosures are hereby incorporated by reference.

BACKGROUND

1. Technical Field

The present disclosure relates to spinal fixation constructs and, more specifically, to spinal fixation constructs with a flexible member.

2. Discussion of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and rods. Depending on the pathology and treatment, a surgeon will select the appropriate spinal rod material and size, specifically, the cross-sectional diameter.

One growing trend seen post-surgical treatment of a patient's spine is the incidence of proximal junctional kyphosis (PJK), which is typically an adult spinal deformity surgical outcome if the lumbar lordosis and thoracic kyphosis are not properly restored post-surgery. PJK appears at or above the cranial-most thoracic level treated. Even though PJK most commonly occurs in the thoracic region of the spine, it can also occur in various spinal regions and may occur above or below the instrument levels and may impact the next adjacent level or two that is not instrumented. This type of failure is called adjacent level failure. Symptoms of PJK and adjacent level failure include pain, neurological deficit, ambulatory difficulty and poor maintenance of sagittal balance. For patients that present with these symptoms, often the only treatment is an additional surgery. The incidence rate of PJK may be upward of 50% in long construct, instrumented fusion cases. Factors contributing to this condition are the end vertebrae selection, facet violation, weakened structural support due to significant soft tissue disruption, extensive junctional paraspinal musculature dissection and loss of integrity of the posterior tension band.

One thought to address the problem of PJK, which is caused by the accelerated degeneration of the joint capsules and smaller articular processes at one or two levels above or below the junctional region, is to decrease the structural rigidity of the construct at the top of the construct just below the proximal junction, thereby providing a transition from the relatively stiff instrumented spine to the more flexible non-instrumented spine.

Spinal rods are typically made of cobalt chrome, stainless steel, or titanium alloy. However in order to transition to a less stiff construct at the top, other less rigid materials may be employed to provide the desired stiffness. A continuing need exists for an improved device, an improved system, and an improved method for performing spine surgery that does not create additional morbidity post-surgical treatment.

SUMMARY

The present disclosure relates to a spinal construct including a rigid portion and a flexible portion. The flexible portion can be positioned in a cephalad direction and/or a caudal direction relative to the rigid portion. The flexible portion transitions a portion of a load from the rigid portion of the spinal construct to the patient's anatomy to reduce the load on an uninstrumented vertebral level adjacent the rigid portion. It is envisioned that by reducing the load on the uninstrumented vertebral level adjacent the rigid portion of the spinal construct, instances of PJK can be reduced.

In an aspect of the present disclosure, a fixation member includes a head and a shank. The shank defines a longitudinal axis of the fixation member and the head defines a slot that passes through the head orthogonal to the longitudinal axis. The slot is configured to receive a flexible member.

In aspects, the head includes a retention bar that passes over the slot. The retention bar may be configured to receive a flexible member thereabout.

In another aspect of the present disclosure, a system for securing a flexible member to a vertebra includes a flexible member, a fixation member, and an inserter. The flexible member has two ends and a central portion between the ends. The fixation member includes a head and a shank. The shank defines a longitudinal axis of the fixation member and the head defines a slot that passes through the head orthogonal to the longitudinal axis. The slot receives the central portion of the flexible member. The inserter includes a handle and a tubular member. The tubular member has a proximal end portion that is attached to the handle and a distal end portion that extends from the handle. The tubular member defines a passage between the proximal and distal end portions. The distal end portion includes a coupler for receiving the head of the fixation member with the central portion of the flexible member received in the slot of the fixation member. The flexible member passes through the passage of the tubular member and into a groove defined in an outside surface of the handle.

In aspects, when the head is received within the coupler, the shank of the fixation member is rotatably fixed to the inserter.

In some aspects, the handle includes a securement member that is pivotally coupled to the handle for selectively fixing the flexible member within the groove of the handle. The securement member may be a lever that includes a grip. The securement member may have a secured position in which the grips is adjacent the handle such that the flexible member is fixed within the groove and an unsecured position in which the grip is spaced apart from the handle such that the flexible member is slidable within the groove. In the secured position of the securement member, the grip may engage the flexible member.

In certain aspects, the groove extends from a proximal end of the handle towards a distal end of the handle. The ends of the flexible member may extend into the grove from an opening defined in the proximal end of the handle.

In another aspect of the present disclosure, a method of securing a flexible member to a bony element includes attaching the flexible member to a head of a fixation member, rotatably fixing the head of the fixation member in a coupler of an inserter with the flexible member attached to the head, fixing the flexible member within a groove of a handle of the inserter to secure the fixation member to the inserter, engaging a bone element with a shank of the fixation member secured to the inserter, and driving the fixation member into the bony element with the inserter.

In aspects, attaching the flexible member to the head of the fixation member includes passing an end of the flexible member through a slot defined in the head of the fixation member. Fixing the flexible member within the groove of the handle may include passing ends of the flexible member through the groove of the handle such that a central portion of the flexible members is disposed within the groove with a securement member in an unsecured position and transitioning the securement member to a secured position to fix the flexible member within the groove. Fixing the flexible member within the groove of the handle may include passing ends of the flexible member through a passage of the tubular member that is engaged with the head of the fixation member. Transitioning the securement member to the secured position may include pivoting the securement member such that a grip of the securement member is pivoted towards the handle. Transitioning the securement member to the secured position may include engaging the flexible member with the grip of the securement member.

In some aspects, the method may include transitioning the securement member to an unsecured position after driving the fixation member into the bony element with the inserter to release the flexible member form the groove of the handle. Transitioning the securement member to the unsecured position includes pivoting a grip of the securement member away from the handle.

In certain aspects, driving the fixation member into the bony element with the inserter includes rotating the inserter.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
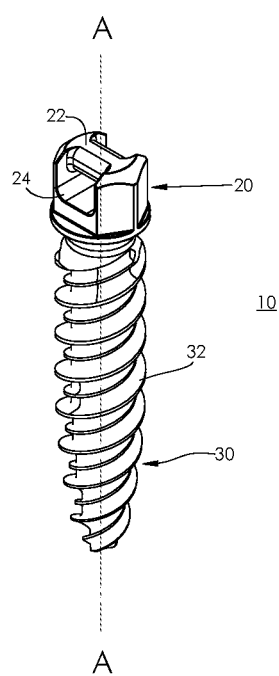
FIG. 1 is a perspective view of an exemplary fixation member provided in accordance with the present disclosure.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

This disclosure relates generally to a spinal fixation construct including a flexible member for tethering a bony element to the spinal construct. The spinal construct includes a fixation member for securing the flexible member to a bony element, an inserter for securing the fixation member in a bony element, and a rigid portion. The spinal construct limits movement in a kyphotic direction while permitting movement in the opposite direction. In addition, a method for installing the spinal construct on a spine of a patient is disclosed.

Referring now to FIG. 1, a fixation member 10 for tethering a flexible member 40 (FIG. 4) to a bony element is described in accordance with the present disclosure. The fixation member 10 includes a head 20 and a shank 30. As shown, the head 20 is hexagonal in shape; however, the head 20 can have any shape suitable for engagement of the inserter 50 (FIG. 2) as described in greater detail below. The head 20 includes a retention bar 22 that defines a slot 24 which passes through the head 20 orthogonal to a longitudinal axis A-A of the fixation member 10 defined by the shank 30. The shank 30 is configured to secure the fixation member 10 in a bony element. As shown, the shank 30 includes threads 32 that threadably engage a bony element to fix the fixation member 10 relative to the bony element. It is envisioned that the head 20 can be moveable relative to the shank 30. For example, the head 20 can be pivotable and/or rotatable relative to the shank 30.

Figure 2:
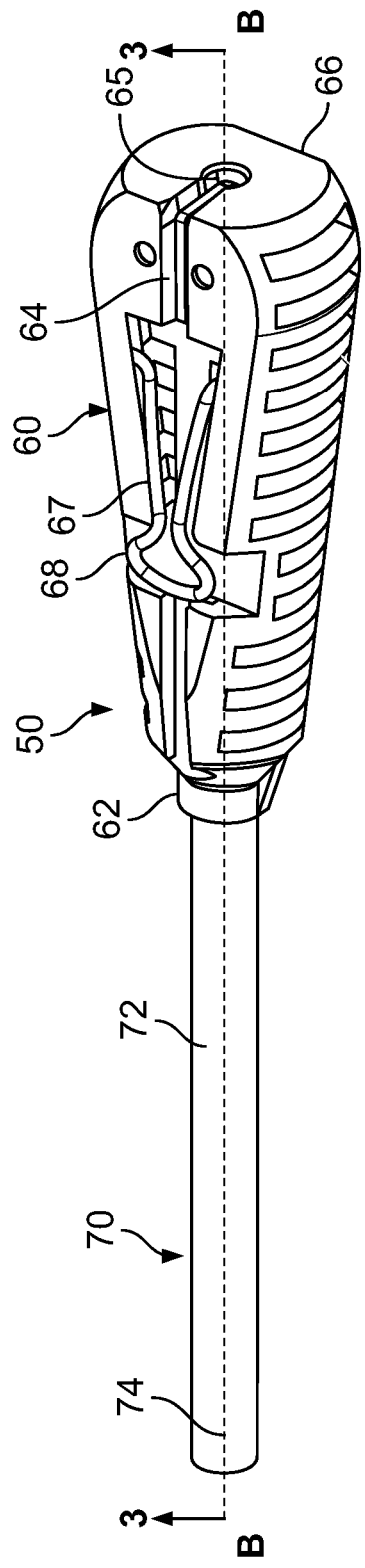
FIG. 2 is a perspective view of an exemplary inserter provided in accordance with the present disclosure.
Figure 3:
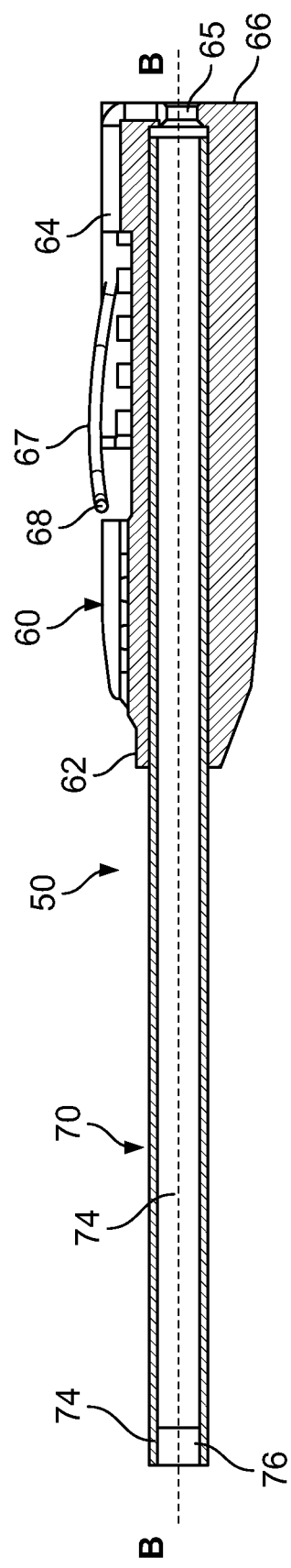
FIG. 3 is a cross-sectional view taken along section line 3-3 of FIG. 2.

Referring now to FIGS. 2 and 3, an inserter 50 for securing the fixation member 10 in a bony element with a flexible member 40 (FIG. 4) attached to the fixation member 10 (FIG. 1) is described in accordance with the present disclosure. The inserter 50 includes a handle 60 and a tubular member 70 extending from the handle 60. The tubular member 70 includes a proximal end portion 72 and a distal end portion 74. The tubular member 70 defines an axis B-B and a passage 78 about the axis B-B between the proximal and distal end portions 72, 74. The proximal end portion 72 is coupled to the handle 60. As shown, the proximal end portion 72 is threadably coupled to a connector 62 of the handle 60; however, the proximal end portion 72 can be welded, adhered, or joined to the handle 60 by a variety of known suitable methods.

The distal end portion 74 of the tubular member 70 defines a coupler 76 for releasably engaging the head 20 (FIG. 1) of the fixation member 10. The coupler 76 is sized and dimensioned to receive the head 20 such that the head 20 is rotatably fixed to the tubular member 70. For example, when the head 20 is hexagonal in shape, as described above, the coupler 76 may define a hexagonal opening such that each face of the head 20 is fully engaged with a wall defining the coupler 76. Alternatively, when the head 20 is hexagonal in shape, the coupler 76 may be a dodecagonal opening such that a portion of each face of the head 20 is engaged with a wall defining the coupler 76. It is contemplated that the connection between the head 20 and the inserter 50 can be a friction fit, a press fit, a snap fit, a snap into, a snap over, a clip in, a magnetic, or other known suitable means for releasably attaching two members.

The coupler 76 is in communication with the passage 78 such that the flexible member 40 (FIG. 4) can pass through the slot 24 of the head 20 and the passage 78 of the tubular member 70 when the head 20 is received within the coupler 76.

The handle 60 defines a longitudinal groove 64 in an outer surface thereof that receives the flexible member 40 as detailed below. As shown, a proximal end 66 of the handle 60 defines an opening 65. The groove 64 is aligned with the opening 65 such that the flexible member 40 can pass from the opening 65 into the groove 64 about the proximal end 66 as described in greater detail below.

Figure 4:
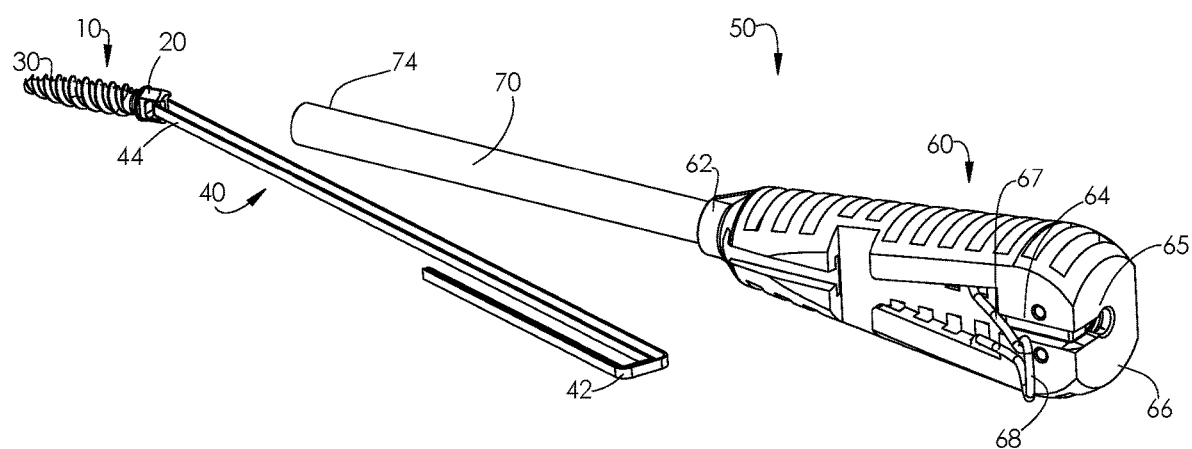
FIG. 4 is a perspective view of a system for securing a flexible member to a bony element including the fixation member of FIG. 1 and the inserter of FIG. 2.

With additional reference to FIG. 4, the handle 60 includes a securement member 67 that selectively secures the flexible member 40 within the groove 64. As shown, the securement member 67 is a lever that is pivotally coupled to the handle 60 and has a grip 68. The securement member 67 is movable between a secured position (FIG. 2) in which the grip 68 of the securement member 67 is adjacent or in contact with the handle 60. In the secured position of the securement member 67, the grip 68 is positioned within the groove 64 to secure the flexible member 40 within the groove 64 and prevent the flexible member 40 from withdrawing through the passage 78 as detailed below. The securement member 67 also has an unsecured position (FIG. 4) in which the grip 68 of the securement member 67 is spaced apart from the handle 60 such that the flexible member 40 is moveable within the groove 64 and the passage 78. It is envisioned that the securement member 67 is biased towards the secured position.

Additionally or alternatively, the handle 60 can include other means for preventing the flexible member 40 from withdrawing through the passage 78. For example, the handle 60 can include a clip or cleat (not shown) that is attached to the ends of the flexible member 40 to prevent the flexible member 40 from withdrawing through the passage 78. It is contemplated that the handle 60 can include a capstan, cam cleat, or tab and slot arrangement to secure the flexible member 40 within the groove 64 and prevent the flexible member 40 from withdrawing through the passage 78.

With reference to FIGS. 4-7, a method of securing the fixation member 10 in a bony element with the inserter 50 is described in accordance with the present disclosure. Initially referring to FIG. 4, the flexible member 40 is passed through the slot 24 (FIG. 1) of the fixation member 10 to attach the flexible member 40 to the head 20 of the fixation member 10. The flexible member 40 includes ends 42 and a center section 44 therebetween. When the flexible member 40 is attached to the head 20, the center section 44 of the flexible member 40 is wrapped around the retention bar 22 of the head 20 (FIG. 1).

Figure 5:
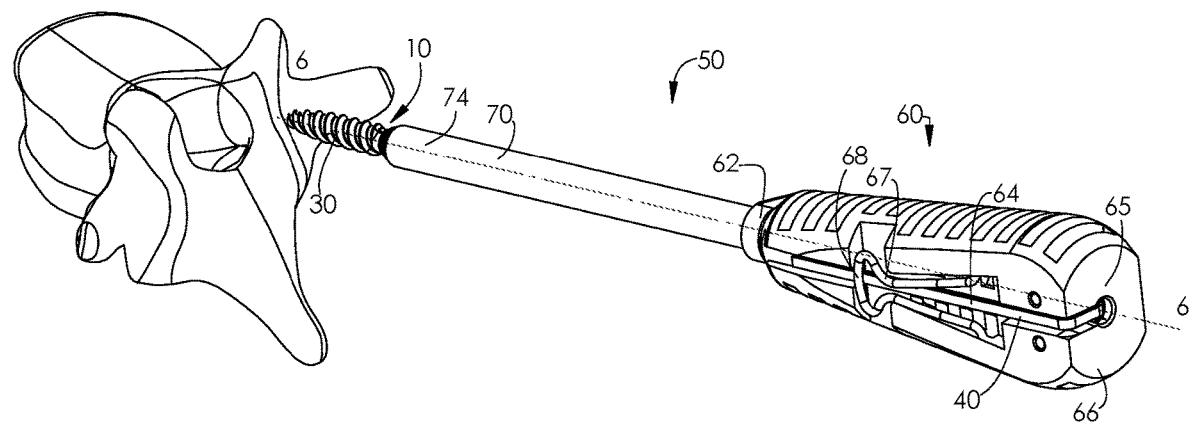
FIG. 5 is a perspective view of the system of FIG. 4 with the fixation member secured to the inserter.
Figure 6:
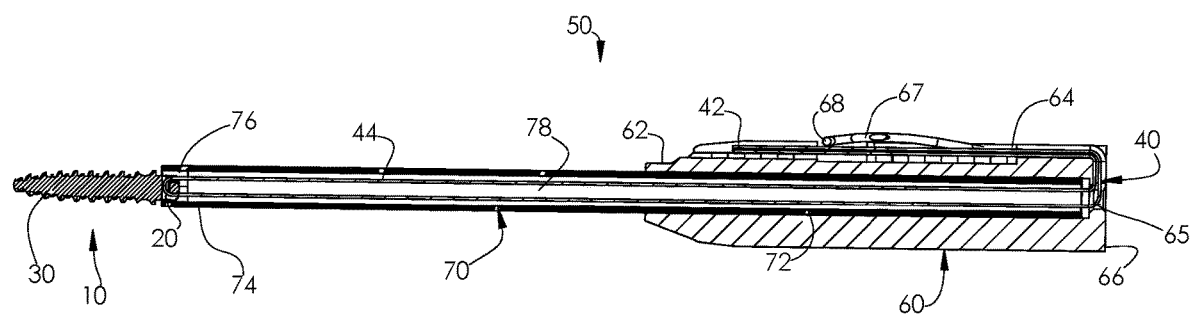
FIG. 6 is a cross-sectional view taken along section line 6-6 of FIG. 5.

Continuing to refer to FIG. 4, with the flexible member 40 secured to the head 20, the ends 42 of the flexible member 40 are passed through the passage 78 of the tubular member 70, out the opening 65, and into the groove 64 of the handle 60 with the securement member 67 in the unsecured position. With the securement member 67 in the unsecured position, the ends 42 of the flexible member 40 can slide within the groove 64 and under the securement member 67. The ends 42 of the flexible member 40 are drawn through until the head 20 of the fixation member 10 is within the coupler 76 of the tubular member 70 as shown in FIGS. 5 and 6. With the head 20 within the coupler 76 of the tubular member 70, the ends 42 of the flexible member 40 are drawn until the flexible member 40 is taut from the head 20, through the passage 78, and within the groove 64.

With the flexible member 40 drawn taut, the securement member 67 is pivoted to the secured position as shown in FIG. 5. When the securement member 67 is pivoted to the secured position, the grip 68 of the securement member 67 engages the flexible member 40 to secure the flexible member 40 within the groove 64 as shown in FIG. 6. When the flexible member 40 is secured within the groove 64, the flexible member 40 is fixed relative to the handle 60 and prevented from withdrawing through the passage 78 of the tubular member 70. It will be appreciated that when the flexible member 40 is taut and fixed relative to the handle 60, the head 20 of the fixation member 10 is secured within the coupler 76 of the inserter 50.

With continuing reference to FIGS. 5 and 6, with the head 20 of the fixation member 10 secured in the coupler 76 of the inserter 50, the inserter 50 is used to secure the fixation member 10 into a bony element. Specifically, the inserter 50 is positioned such that the shank 30 of the fixation member 10 engages a bony element. With the shank 30 engaging the bony element, the inserter 50 is rotated to affect rotation of the shank 30 such that the shank 30 is threaded into the bony element. It is contemplated that a pilot hole can be drilled in the bony element to assist in threading the shank 30 into the bony element.

Figure 7:
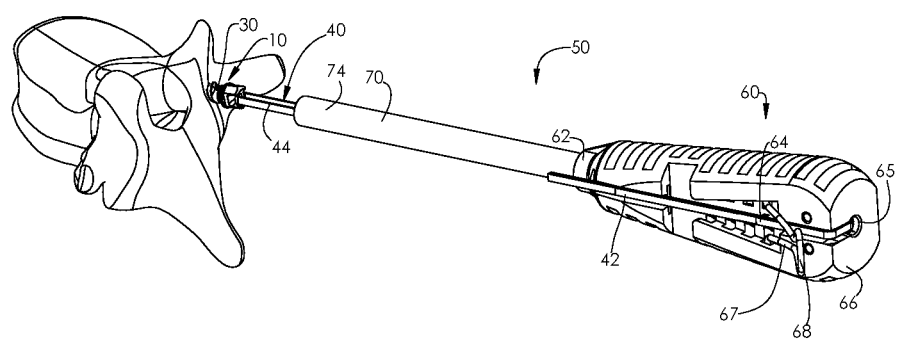
FIG. 7 is a perspective view of the fixation member of FIG. 4 secured to a bony element with the flexible member attached to the fixation member.
Figure 8:
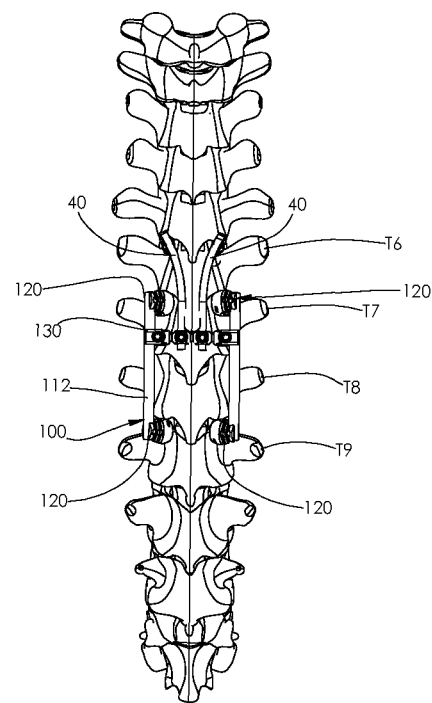
FIG. 8 is a posterior view of a partial spinal column with a spinal construct attached in accordance with the present disclosure.
Figure 9:
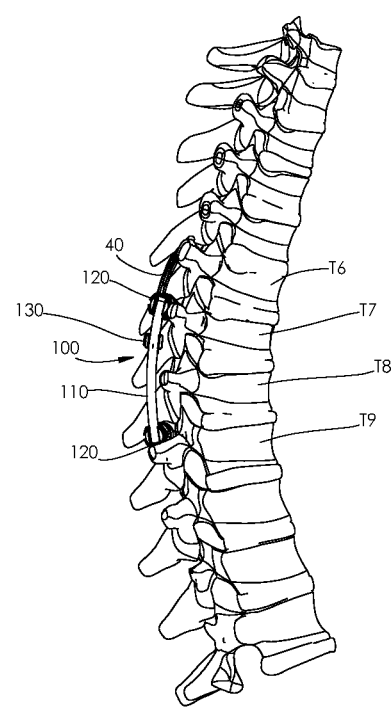
FIG. 9 is a side view of the partial spinal column of FIG. 8.

When a desired length of the shank 30 is threaded into the bony element, the inserter 50 is withdrawn from over the head 20 of the fixation member 10 as shown in FIG. 7. It will be appreciated that the securement member 67 may be pivoted towards the unsecured configuration to permit the flexible member 40 to slide from within the groove 64 of the handle 60 and through the passage 78 of the tubular member 70.

With the fixation member 10 secured to a bony element and inserter 50 withdrawn such that the flexible member 40 free from within the passage 78, the flexible member 40 is attached to a spinal construct to limit movement of the bony element relative to another bony element as detailed below.

Figure 11:
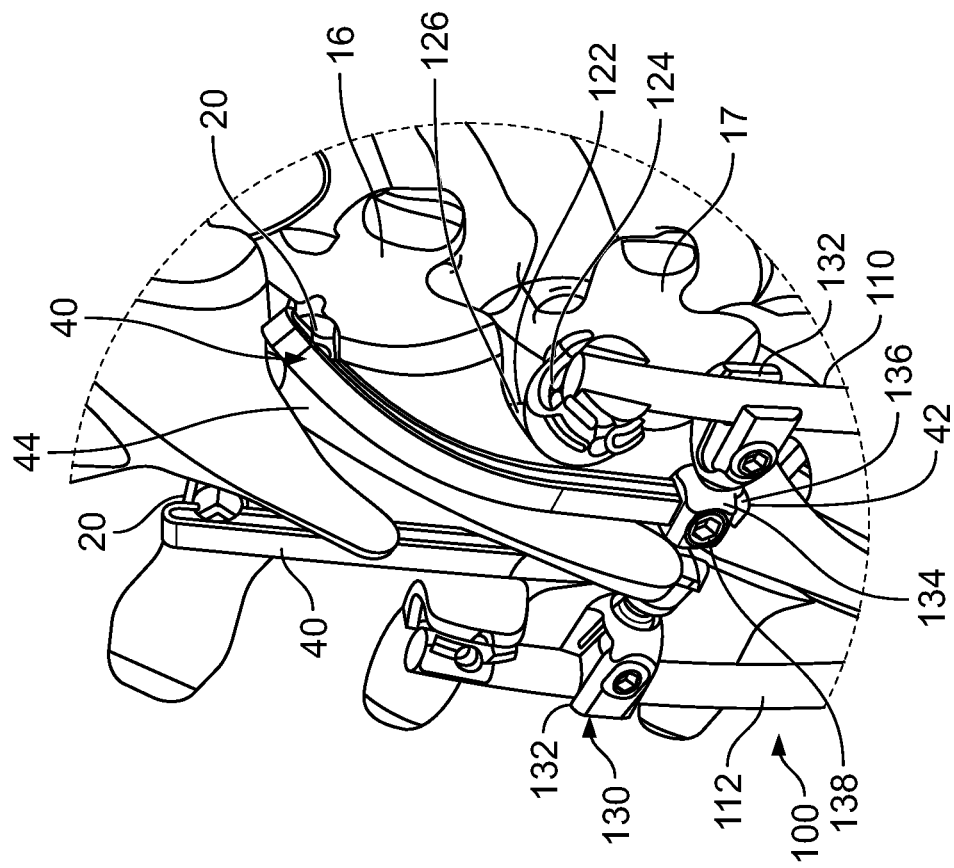
FIG. 11 is an enlarged view of the indicated area of detail of FIG. 10.
Figure 10:
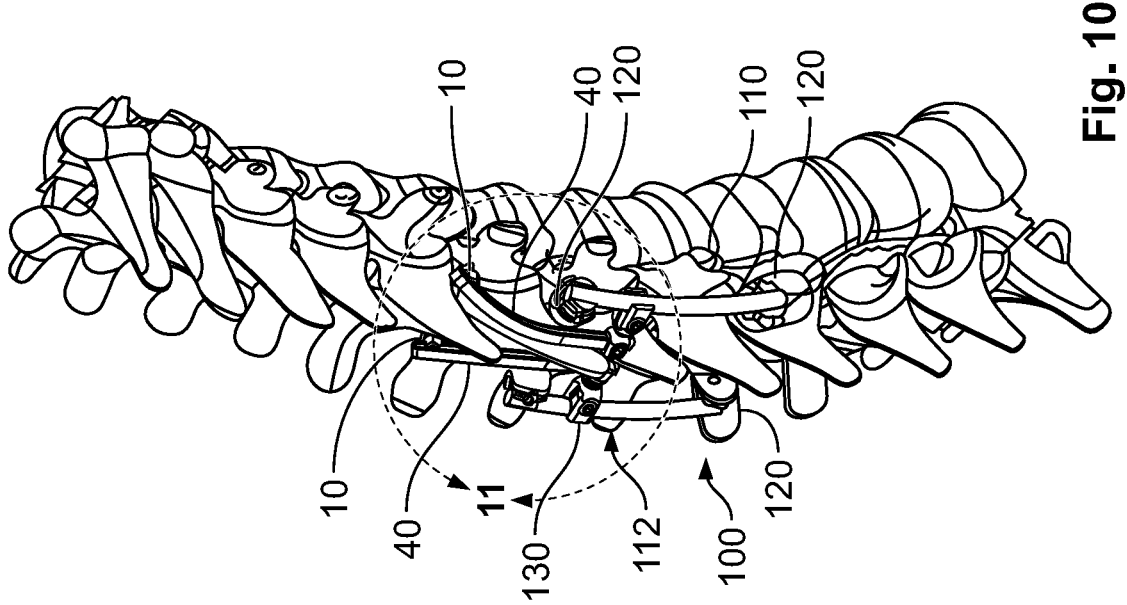
FIG. 10 is a posterior perspective view of the partial spinal column of FIG. 8.

With reference to FIGS. 8-11, the flexible member 40 is attached to a rigid portion of a spinal construct 100 that is secured to vertebrae in a thoracic portion of the spine. Specifically, the spinal construct 100 includes two spinal rods 110, 112 that are secured on either side of a spinous process of vertebrae T7 and T8 by pedicle screws 120. As shown, each of the pedicle screws 120 includes a head 122 and a shank 126 (FIG. 11). The shank 126 of each pedicle screw 120 is secured in a respective vertebra. The head 122 defines a saddle 124 that receives the one of the spinal rods 110, 112 to secure a respective one of the spinal rods 110, 112 to the head 122. As shown, the head 122 is a taper-lock style head to secure the respective spinal rod 110, 112 within the saddle 124. It is contemplated that other known means for securing the respective spinal rod 110, 112 within the saddle 124 may also be used including, but not limited to, a set screw (not shown) threadably engaged with the saddle 124.

The spinal construct 100 also includes a cross-connector 130 that interconnects the spinal rods 110, 112. The cross-connector 130 includes saddles 132 that secure the cross-connector 130 to the spinal rods 110, 112. The cross-connector 130 also includes retainers 134 positioned between the saddles 132. Each of the retainers 134 define a retention slot 136 and includes a retention screw 138.

For detail descriptions of exemplary pedicle screws reference can be made to U.S. Pat. No. 8,403,971, filed Apr. 23, 2010, and U.S. Pat. No. 8,814,919, filed Apr. 23, 2010. For detailed descriptions of exemplary cross-connectors reference can be made to U.S. Pat. No. 8,961,565, filed Aug. 23, 2010. For detailed description of exemplary retainers reference can be made to U.S. Provisional Patent Application Ser. No. 62/152,325, filed Apr. 24, 2015, entitled "Tethering Screw System." The entire contents of each of these disclosures are incorporated by reference.

Alternatively, it is envisioned that the flexible member 40 may be secured about a bony element. The ends 42 of the flexible member 40 may pass through a clamp (not shown) before being secured to the cross-connector 130. For detailed descriptions of exemplary clamps, reference can be made to U.S. Patent Publication No. 2014/0257397, filed Mar. 11, 2014, the entire disclosure of which is incorporated by reference.

With particular reference to FIG. 11, each of the flexible members 40 is secured to a respective retainer 134 of the cross-connector 130 that is on the same side of the spinous process as the fixation member 10 associated with the flexible member 40. The ends 42 of the flexible member 40 are passed through the retention slot 136 of the respective retainer 134 such that the central portion 44 of the flexible member 40 forms a loop between the retainer 134 and the head 20 of the fixation member 10. The size of the loop can be adjusted to allow a desired amount of kyphotic movement while preventing excessive kyphodic movement between the spinal construct 100 and the vertebra engaged by the fixation member 10. After the size of the loop is adjusted, the retention screw 138 is used to secure the central portion 44 of the flexible member 40 in the retainer 134 which fixes the size of the loop. It will be appreciated that as the vertebrae (e.g., T6 and T7) move relative to one another, the central portion 44 of the flexible member 40 slides through the slot 24 of the head 20 to limit the movement of the vertebrae relative to one another.

The flexible member 40 may be composed of a single material or be a combination of materials. The flexible member 40 is construed from one or more biocompatible materials including, but not limited to, polyethylene, ultra high molecular weight polyethylene (UHMWPE), polypropylene, polyetherimide, poly sulfone, polyacetal, nylon, poly-ether-ether-ketone (PEEK), polytetraflouroethylene, or combinations thereof. For example, it is envisioned that the flexible member 40 may include a core with a sheath disposed about the core. It is contemplated that the flexible member may be braid in various shapes including, but not limited to, a round braid or a flat braid. For detail descriptions of exemplary flexible members and uses thereof reference can be made to U.S. patent application Ser. No. 14/644,428, filed Mar. 11, 2015, the entire contents of which are incorporated by reference.

As detailed above, the spinal construct 100 is attached to the thoracic portion of a spinal column; however, it is envisioned that the spinal construct can be attach anywhere along the spinal column with the fixation members 10 and flexible members 40 attached to a vertebra adjacent to or spaced apart from the rigid portion of the spinal construct 100 in a cephalad direction and/or a caudal direction.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

The invention claimed is:

1. A method of securing a flexible member to a spinal bone, the method comprising:
    embedding an anchor into a first vertebra of a spine with an inserter, the anchor having a first portion of the flexible member attached thereto such that a second portion of the flexible member extends away from the anchor;

securing the second portion of the flexible member to the inserter by pivoting a securement member coupled to the inserter to clamp the flexible member to the inserter; and securing the second portion of the flexible member to a spinal construct affixed to the spine.

2. The method of claim 1, wherein securing the second portion of the flexible member to the inserter comprises pivoting the securement member coupled to the inserter from an unsecured position to a secured position to clamp the flexible member to the inserter.

3. The method of claim 1, further comprising passing the second portion of the flexible member through a slot of a retainer of the spinal construct.

4. The method of claim 3, wherein the securing step further comprises securing the second portion of the flexible member within the slot by rotatably engaging a retention screw of the retainer.

5. The method of claim 1, further comprising attaching the first portion of the flexible member to the anchor.

6. The method of claim 5, wherein attaching the first portion of the flexible member to the anchor comprises passing the flexible member through a slot defined in a head of the anchor.

7. The method of claim 1, wherein the securing step includes securing the second portion of the flexible member between a first longitudinal rod and a second longitudinal rod secured to the spine on opposite sides of a spinous process of the first vertebra.

8. The method of claim 7, wherein the securing step includes securing the second portion of the flexible member to a cross-connector coupled to and extending between the first and second longitudinal rods.

9. The method of claim 1, wherein the first portion comprises a loop attached to the anchor, and the flexible member includes a third portion extending away from the first portion, and wherein the securing step further comprises securing the second and third portions to the spinal construct.

10. The method of claim 1, wherein the embedding step further comprises rotatably securing a threaded portion of the anchor into the first vertebra of the spine.

11. A method of securing a flexible member to a spinal bone, the method comprising:
engaging a first portion of the member to a portion of a first vertebra of a spine with an inserter such that a second portion of the flexible member extends away from the portion of the first vertebra;
securing the second portion of the flexible member to the inserter by pivoting a securement member coupled to the inserter to clamp the flexible member to the inserter; and
securing the second portion of the flexible member to a cross-connector of a spinal construct affixed to the spine, the cross-connector coupled to and extending between two longitudinal rods of the spinal construct.

12. The method of claim 11, further comprising passing the second portion of the flexible member through a slot of a retainer of the cross-connector.

13. The method of claim 12, wherein the securing step further comprises securing the second portion of the flexible member to the slot by rotatably engaging a retention screw of the retainer.

14. The method of claim 11, wherein the first portion comprises a loop attached to the portion of the first vertebra, and the flexible member includes a third portion extending away from the first portion, and wherein the securing step further comprises securing the second and third portions to the cross-connector.

15. The method of claim 11, wherein engaging a first portion of a flexible member to a portion of a first vertebra of a spine comprises embedding an anchor into a first vertebra of a spine, the anchor having the first portion of the flexible member attached thereto.

16. The method of claim 15, further comprising attaching the first portion of the flexible member to the anchor.

17. The method of claim 16, wherein attaching the first portion of the flexible member to the anchor comprises passing the flexible member through a slot defined in a head of the anchor.

18. The method of claim 11, wherein securing the second portion of the flexible member to the inserter comprises pivoting the securement member coupled to the inserter from an unsecured position to a secured position to clamp the flexible member to the inserter.

19. A method of securing a flexible member to a spinal bone, the method comprising:
embedding an anchor into a first vertebra of a spine with an inserter, the anchor having a first portion of the flexible member attached thereto such that a second portion of the flexible member extends away from the anchor;
securing the second portion of the flexible member to the inserter by moving a securement member from an unsecured position to a secured position to clamp the flexible member to the inserter, wherein at least a portion of the securement member is translationally fixed to the inserter in a same location in both the unsecured position and the secured position; and
securing the second portion of the flexible member to a spinal construct affixed to the spine.

* * * * *